(12) United States Patent
Rabizadeh et al.

(10) Patent No.: US 7,994,184 B2
(45) Date of Patent: Aug. 9, 2011

(54) SMALL MOLECULES THAT REPLACE OR AGONIZE P53 FUNCTION

(75) Inventors: Shahrooz Rabizadeh, Novato, CA (US); Kayvan Niazi, Novato, CA (US); Dale E. Bredesen, Novato, CA (US)

(73) Assignee: Buck Institute, Novato, CA (US)

( * ) Notice: Subject to any disclaimer, the term of this patent is extended or adjusted under 35 U.S.C. 154(b) by 416 days.

(21) Appl. No.: 11/203,609

(22) Filed: Aug. 12, 2005

(65) Prior Publication Data

US 2006/0094738 A1   May 4, 2006

Related U.S. Application Data

(60) Provisional application No. 60/603,308, filed on Aug. 20, 2004.

(51) Int. Cl.
*A61K 31/505* (2006.01)

(52) U.S. Cl. ........................ 514/275; 514/256

(58) Field of Classification Search .................. 514/275, 514/256
See application file for complete search history.

(56) References Cited

U.S. PATENT DOCUMENTS

| | | | |
|---|---|---|---|
| 4,698,176 A * | 10/1987 | Gray et al. | 252/299.61 |
| 4,699,789 A * | 10/1987 | Schultz | 424/147.1 |
| 4,844,911 A * | 7/1989 | Kakimoto et al. | 426/11 |
| 5,010,175 A | 4/1991 | Rutter et al. | |
| 5,288,514 A | 2/1994 | Ellman | |
| 5,506,337 A | 4/1996 | Summerton et al. | |
| 5,519,134 A | 5/1996 | Acevedo et al. | |
| 5,525,735 A | 6/1996 | Gallop et al. | |
| 5,539,083 A | 7/1996 | Cook et al. | |
| 5,549,974 A | 8/1996 | Holmes | |
| 5,569,588 A | 10/1996 | Ashby et al. | |
| 5,593,853 A | 1/1997 | Chen et al. | |
| 5,744,310 A | 4/1998 | Reed | |
| 5,837,838 A | 11/1998 | Reed et al. | |
| 5,856,362 A * | 1/1999 | Hudson | 514/682 |
| 6,228,850 B1 * | 5/2001 | Jaggi et al. | 514/169 |
| 6,235,714 B1 | 5/2001 | Paul et al. | |
| 6,274,732 B1 * | 8/2001 | Cho et al. | 544/312 |
| 6,479,466 B1 * | 11/2002 | Redfield et al. | 514/45 |
| 6,693,194 B2 * | 2/2004 | Jau et al. | 544/302 |

FOREIGN PATENT DOCUMENTS

| | | | |
|---|---|---|---|
| JP | 6 256113 | * | 9/1994 |
| WO | WO-91/19735 A1 | | 12/1991 |
| WO | WO-92/00091 A1 | | 1/1992 |
| WO | WO-93/20242 A1 | | 10/1993 |
| WO | WO 95/19367 A | | 7/1995 |
| WO | WO-97/00271 A1 | | 1/1997 |
| WO | WO-2006/023410 A2 | | 3/2006 |

OTHER PUBLICATIONS

Baker et al. Journal of Medicinal Chemistry (1969), 12(1), 74-8.*

(Continued)

*Primary Examiner* — Sharmila G. Landau
*Assistant Examiner* — Kortney L Klinkel
(74) *Attorney, Agent, or Firm* — Morrison & Foerster LLP

(57) ABSTRACT

This invention provides a novel screening system for identifying p53 mimetics/agonists. Also provided are small organic molecules that act as effective p53 mimetics/agonists.

12 Claims, 10 Drawing Sheets

OTHER PUBLICATIONS

Baker et al. Irreversible enzyme inhibitors. CXXXIV. Effect of ring substitution on the selective irreversible inhibition of dihydrofolic reductase from L1210 mouse leukemia and liver by 2,4-diamino-5-(3,4-dichlorophenyl)-6-[p-(m-fluorosulfonylphenylureido)phenoxymethyl]pyrimidine, Jan. 1969.*

Choi et al. Identification of highly potent and selective inhibition of *Toxoplasma gondii* dihydrofolase reductase. Antimicrobial Agents and Chemotherapy. 1993;37(9): 1914-1923.*

Baker et al. J. Med. Chem. 1968, 11, 495-500.*

Xu et al. "Statistical cluster analysis of pharmaceutical solvents", International Journal of Pharmaceutics, 2007, 229, 175-188.*

Baum, R. (Jan. 18, 1993). "Solid-Phase Synthesis of Benzodiazepines," *C&EN*, pp. 33-34.

Campbell, D.A. et al. (Feb. 11, 1994). "Phosphonate Ester Synthesis Using a Modified Mitsunobu Condensation," *J. Org. Chem.* 59(3):658-660.

Chen, C. et al. (Mar. 23, 1994). "'Analogous' Organic Synthesis of Small-Compound Libraries: Validation of Combinatorial Chemistry in Small-Molecule Synthesis," *J. Am. Chem. Soc.* 116(6):2661-2662.

Cho, C.Y. et al. (Sep. 3, 1993). "An Unnatural Biopolymer," *Science* 261(5126):1303-1305.

Dewitt, S. H. et al. (Aug. 1993). "'Diversomers': An Approach to Nonpeptide, Nonoligomeric Chemical Diversity," *Proc. Natl. Acad. Sci. USA* 90:6909-6913.

Furka, Á. (Jun. 1991). "General Method for Rapid Synthesis of Multicomponent Peptide Mixtures," *Int. J. Pept. Prot. Res.* 37(6):487-493.

Gallop, M.A. et al. (Apr. 29, 1994). "Applications of Combinatorial Technologies to Drug Discovery. 1. Background and Peptide Combinatorial Libraries," *J. Med. Chem.* 37(9):1233-1251.

Gordon, E.M. et al. (May 13, 1994). "Applications of Combinatorial Technologies to Drug Discovery. 2. Combinatorial Organic Synthesis, Library Screening Strategies, and Future Directions," *J. Med. Chem.* 37(10):1385-1401.

Hagihara, M. et al. (Jul. 29, 1992). "Vinylogous Polypeptides: An Alternative Peptide Backbone," *J. Am. Chem. Soc.* 114(16):6568-6470.

Hirschmann, R. et al. (Nov. 4, 1992). "Nonpeptidal Peptidomimetics with a β-D-Glucose Scaffolding. A Partial Somatostatin Agonist Bearing a Close Structural Relationship to a Potent, Selective Substance P Antagonist," *J. Amer. Chem. Soc.* 114(23):9217-9218.

Houghton, R.A. et al. (Nov. 7, 1991). "Generation and Use of Synthetic Peptide Combinatorial Libraries for Basic Research and Drug Discovery," *Nature* 354(6348):84-87.

Krajewski, S. et al. (Oct. 1, 1995). "Reduced Expression of Proapoptotic Gene *BAX* is Associated with Poor Response Rates to Combination Chemotherapy and Shorter Survival in Women with Metastatic Breast Adenocarcinoma," *Cancer Res.* 55:4471-4478.

Lai, H. et al. (Jan. 1, 2004). "Spectrum of p53 Tumor Suppressor Gene Mutations and Breast Cancer Survival," *Breast Cancer Res. Treat.* 83(1):57-66.

Liang, R. et al. (Nov. 29, 1996). "Parallel Synthesis and Screening of a Solid Phase Carbohydrate Library," *Science* 274:1520-1522.

Miyashita, T. et al. (Jan. 27, 1995). "Tumor Suppressor p53 is a Direct Transcriptional Activator of the Human *bax* Gene," *Cell* 80:293-299.

Reed, J.C. (1996). "Balancing Cell Life and Death: Bax, Apoptosis, and Breast Cancer," *J. Clin. Invest.* 97(11):2403-2404.

Vaughan, T.J. et al. (Mar. 1996). "Human Antibodies with Sub-nanomolar Affinities Isolated from a Large Non-immunized Phage Display Library," *Nat. Biotechnol.* 14(3):309-314.

International Search Report mailed on Jun. 5, 2008, for PCT/US05/28857, filed on Aug. 12, 2005, four pages.

Written Opinion mailed on Jun. 5, 2008, for PCT/US05/28857, filed on Aug. 12, 2005, four pages.

Bargou, R.C. et al. (Jun. 1996). "Overexpression of the Death-promoting Gene bax-α Which is Downregulated in Breast Cancer Restores Sensitivity to Different Apoptotic Stimuli and Reduces Tumor Growth in SCID Mice," *J. Clin. Invest.* 97(11):2651-2659.

Baker, B.R. et al. (Jan. 1, 1970). "Irreversible Enzyme Inhibitors. CLXVI. Active-Site-Directed Irreversible Inhibitors of Dihydrofolic Reductase derived from 2,4-Diamino-5-(3,4-Dichlorophenyl) Pyrimidine with 6 Substitutents and Some Factors in Their Cell Wall Transport," *J. Med. Chem.* 13(1):82-86.

Bykov, V. J. N. et al. (Sep. 1, 2003). "Small Molecules that Reactivate Mutant p53," *European Journal of Cancer* 39(13):1828-1834.

Choudhuri, T. et al. (Feb. 13, 2002). "Curcumin Induces Apoptosis in Human Breast Cancer Cells Through p53-Dependent Bax Induction," *FEBS Letters* 512(1-3):334-340.

Liontas, A. et al. (Mar. 1, 2004). "Curcumin and Resveratrol Induce Apoptosis and Nuclear Translocation and Activation of p53 in Human Neuroblastoma," *Anticancer Research*, 24(2B):987-998.

Lin, H.-Y. et al. (Aug. 1, 2002). "Resveratrol Induced Serine Phosphorylation of p53 Causes Apoptosis in a Mutant p53 Prostate Cancer Cell Line," *Journal of Urology* 168(2):748-755.

Watabe, M. et al. (Feb. 13, 2004). "Caffeic Acid Phenethyl Ester Induces Apoptosis by Inhibition of NFkappaB and Activation of Fas in Human Breast Cancer MCF-7 Cells," *J. Biol. Chem.* 279(7):6017-6026.

Supplementary European Search Report mailed Oct. 13, 2009, for European Patent Application No. 05786671.7 filed on Aug. 12, 2005 and published under European Publication No. 1 786 430 on May 23, 2007, 9 pages.

European Search Opinion mailed Oct. 13, 2009, for European Patent Application No. 05786671.7 filed on Aug. 12, 2005 and published under European Publication No. 1 786 430 on May 23, 2007, 8 pages.

Baker, B. R. et al. (Jan. 1969). "Irreversible Enzyme Inhibitors. CXXXV. Effect of Ring Substitution on the Selective Irreversible Inhibition of Dihydrofolic Reductase from L1210 Mouse Leukemia and Liver by 2,4-Diamino-5-(3,4-dichlorophenyl)-6-[*p*-(*p*-fluorosulfonylphenylureido)phenoxymethyl]pyrimidine," *J. Med. Chem.* 12(1):79-81.

Business and Professions Code (California) (2010). Section 4127-4127.8, located at http://www.leginfo.ca.gov/cgi-bin/displaycode?section=bpc&group=04001-05000&file=4127-4127. 8, last visited Dec. 6, 2010, 3 pages.

California Code of Regulations (2010). Title 16 entitled "Professional and Vocational Regulations", Division 17 "California State Board of Pharmacy," vol. 21, published by West®, pp. i-iii, pp. 334.5-334.6(c).

Dvorkin, V. M. (May 1985). "Preparation of Liposomes, Using Phase Reversal Technique Excluding Ultrasonic Treatment," original Russian article located in Biokhimiya (publication of the Academy of Sciences of the USSR) vol. 50, No. 5, Part 2, pp. 866-869.

Dvorkin, V. M. (Nov. 20, 1985). "The Production of Liposomes by a Phase Reversal Method Without Ultrasonic Treatment," *Biochemistry* (Moscow), vol. 50, No. 5, Part 2, pp. 736-739, English translation of the Russian original article located in Biokhimiya (publication of the Academy of Sciences of the USSR) vol. 50, No. 5, Part 2, pp. 866-869.

International Conference on Harmonisation of Technical Requirements for Registration of Pharmaceuticals for Human Use (ICH), (Dec. 1997). "Guidance for Industry—Q3C Impurities: Residual Solvents," located at http://www.fda.gov/downloads/RegulatoryInformation/Guidances/ucm128317.pdf, last visited on Dec. 20, 2010, pp. 1-13 for a total of 16 pages.

International Conference on Harmonisation of Technical Requirements for Registration of Pharmaceuticals for Human Use (ICH), (Feb. 2009). "ICH Harmonised Tripartite Guidelines—Impurities: Guideline for Residual Solvents Q3C (R4)," current Step 4 Version dated Feb. 2009, Parent Guideline dated Jul. 17, 1997 (revised PDE for THF and NMP dated Sep. 12, 2002 and Oct. 28, 2002 incorporated in Nov. 2005), pp. 1-21 for a total of 25 pages.

International Conference on Harmonisation of Technical Requirements for Registration of Pharmaceuticals for Human Use (ICH), (Jul. 20, 2000). "Draft Consensus Guideline, Impurities: Residual Solvents (Maintenance) PDE for Tetrahydrofuran," released for Consultation at Step 2 of the ICH Process on Jul. 20, 2000, by the ICH Steering Committee, located at http://www.nihs.go.jp/mhlw/tuuchi/2000/001227-1830/001227-1830e1.pdf, last visited on Dec. 20, 2010, pp. 1-2 for a total of 4 pages.

McDonnell, G. et al. (Jan. 1999). "Antiseptics and Disinfectants: Activity, Action, and Resistance," *Clin. Microb. Rev.* 12(1):147-179, and one page Erratum (p. 227).

Moody, D. E. (1991). "The Effect of Tetrahydrofuran on Biological Systems: Does a Hepatotoxic Potential Exist?" *Drug & Chemical Toxicology* 14(4):319-342.

"Pharmaceutical Compounding—Sterile Preparations," Chapter <797> of The United States Pharmacopeia, (Jan. 1, 2005). The United States Pharmacopeia, The National Formulary, by authority of The United States Pharmacopeial Convention, meeting at Washington, D. C., Apr. 12-16, 2000, USP 28, NF 23, pp. 2461-2477.

"Sterilization and Sterility Assurance of Compendial Articles," Chapter <1211> of The United States Pharmacopeia, (Jan. 1, 2005). The United States Pharmacopeia, The National Formulary, by authority of The United States Pharmacopeial Convention, meeting at Washington, D. C., Apr. 12-16, 2000, USP 28, NF 23, pp. 2740-2745.

"Disinfectants and Antiseptics," Chapter <1072> of The United States Pharmacopeia, (May 1, 2007). The United States Pharmacopeia, The National Formulary, by authority of The United States Pharmacopeial Convention, meeting at Washington, D. C., Mar. 9-13, 2005, vol. 1, USP 30, NF 25, pp. 504-508.

Thompson, C. A. (Sep. 4, 2003). "USP Publishes Enforceable Chapter on Sterile Compounding," *American Society of Health-System Pharmacists*, located at https://www.ashp.org/import/news/HealthSystemPharmacyNews/newsarticle.aspx?id=1363, last visited on Nov. 17, 2010, 5 pages.

US Code of Federal Regulations, (2010). "Current Good Manufacturing Practice for Finished Pharmaceuticals," Title 21, Part 211, pp. 143-164.

US Federal Register, (Dec. 24, 1997). "International Conference on Harmonisation; Guidance on Impurities: Residual Solvents," in Docket No. 97D-0148, vol. 62, No. 47, pp. 67377-67388.

US Food and Drug Administration (Nov. 2003). "Guidance for Industry, Q3C—Tables and List," located at http://www.fda.gov/downloads/Drugs/GuidanceComplianceRegulatoryInformation/Guidances/ucm073395.pdf, last visited on Dec. 20, 2010, pp. 1-8 for a total of 10 pages.

\* cited by examiner

```
  1  cctgctgatc tatcagcaca gattagtttc tgccactttt taaacttcat
 51  attccttttc tttttacaca aacacaaaca ttcgagtcat gactgggtgg
101  ggtggctcaa gcctgtaatc tcagcacttt gggaggccaa ggtgcgagga
                                #2-like
151  tgcttgagtc tgggagttca gagaccagcc tgggcaacat agagagacct
201  catctccaca taaaaagttt taaaaattaa ccaggggcgg tgtagtccca
251  gctactcagg aggctgaggt gggaggcttc agcccgggaa ttccagactg
301  cagtgagcca tgattgggcc actgcactcc agcctgggca acacagtgag
351  accctgtctc aaaaaaaaaa aaaaaaaaa aaaaaaaac aggaaaaaac
401  aaacaaacag aaaagcaggc ctggcgcggt agctcatgcc tgtaatccca
                                                  #1      #2
451  gcgctttgga aggctgagac ggggttatct cttgggctca caagttagag
        #2          #3     _ _#4_ _
501  acaagcctgg gcgtgggcta tattgctaga tccaggtctc tgcaaaaaac
551  aaaaccactc agtttttagt catctataac gtcctgcctg aagcatgct
              ┌──────►Tx                ════════
601  attttgggcc tctgagcttt tgcacttgct aattccttct gcgctgggga
651  gagctcaaac cctgcccgaa acttctaaaa atggtgcctg ataaatgaa
701  ggcattagag ctgcgattgg acgggcggct gttggacggc gccactgctg
751  gcacttatcg ggagatgctc attggacagt cacgtgacgg gaccaaacct
801  cccgagggag cgaggcaggt gcggtcacgt gacccggcgg cgctgcgggg
851  cagcggccat tttgcggggc ggccacgtga aggacgcacg ttcagcgggg
901  ctctcacgtg acccgggcgc gctgcggccg cccgcgcgga cccggcgaga
951  ggcggcggcg ggagcggcgg tgATG...BAX ORF
```

*Fig. 1*

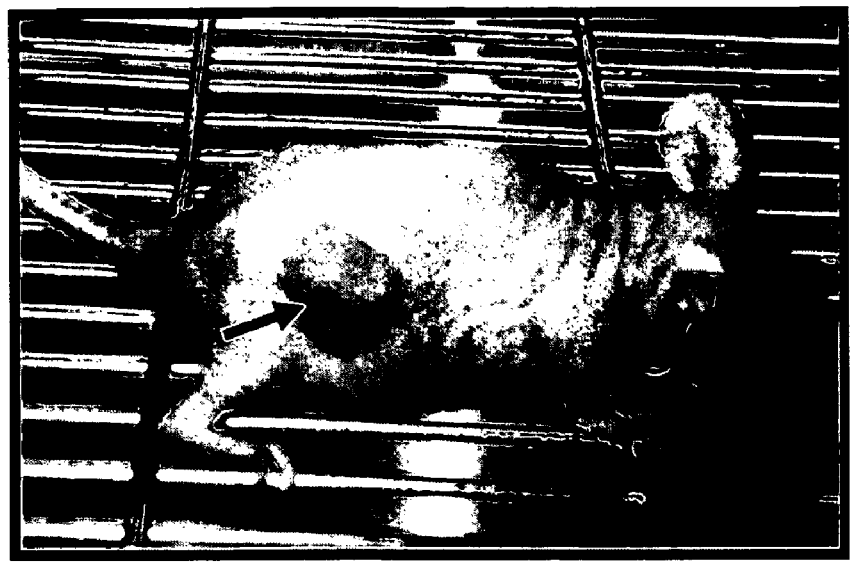
*Fig. 10*

SMALL MOLECULES THAT REPLACE OR AGONIZE P53 FUNCTION

CROSS-REFERENCE TO RELATED APPLICATIONS

This application claims benefit of and priority to U.S. Ser. No. 60/603,308, filed Aug. 20, 2004, which is incorporated herein by reference in its entirety for all purposes.

STATEMENT AS TO RIGHTS TO INVENTIONS MADE UNDER FEDERALLY SPONSORED RESEARCH AND DEVELOPMENT

[NOT APPLICABLE]

FIELD OF THE INVENTION

This invention pertains to the field of oncology. In particular this intention provides compounds that replace and/or agonize p53 function and methods of identifying such compounds.

BACKGROUND OF THE INVENTION

Two-thirds of all breast cancers display mutations in the tumor suppressor p53 (Lai et al. (2004) *Breast Cancer Res. Treat.*, 83: 57-66), and one-third of all advanced human breast carcinomas demonstrate a marked reduction in expression of the pro-apoptotic Bcl-2 family member Bax (Krajewski et al. (1995) *Cancer Res.*, 55: 4471-4478). Bax and p53 mutations are associated with a high percentage of all human tumors. The subgroup of patients displaying p53 mutations or reduced Bax expression generally respond poorly to therapy and exhibit rapidly growing tumors and shorter median survival (Lai et al., supra; Reed (1996) *J. Clin. Invest.*, 97:2403-2404). Though extensively pursued, the mechanism by which Bax expression is regulated in normal, malignant, or dying cells is unknown. The only known endogenous activator of Bax expression is the p53 transcription factor, which is responsible for inducing cell death in cancerous and damaged cells (Miyashita and Reed (1995) *Cell,* 80: 293-299).

SUMMARY OF THE INVENTION

This invention provides novel screening systems well suited for identification of agents that act as p53 mimetics/agonists. Also provided are effective p53 mimetics/agonists.

Thus, in certain embodiments, this invention provides compounds that promote cell death in a p53 naive cell (e.g. a tumor cell). Certain preferred compounds are those of Formula I herein, where $R^1$ and $R^4$ are independently selected from the group consisting of an amino group, a cyano group, a nitro group, a carboxyl group, halo, hydroxyl, $SO_2$, $C_{1-6}$ alkyl, $C_{1-6}$ haloalkyl, $C_{1-8}$ alkoxyl, $C_{1-11}$ alkoxyalkyl, $C_{1-6}$ alkylamino, $C_{1-6}$ aminoalkyl, and the like; $R^2$ and $R^3$ are independently selected from the group consisting of CH, N, and the like; $R^5$ is $CH_2$ or O; $R^6$ and $R^7$ are independently selected from the group consisting of H, halogen, CN, $NO_2$, $C_{1-10}$ branched or unbranched saturated or unsaturated alkyl, $C_{1-10}$ branched or unbranched alkoxy, $C_{1-10}$ branched or unbranched acyl, $C_{1-10}$ branched or unbranched acyloxy, $C_{1-10}$ branched or unbranched alkylthio, aminosulfonyl, aryl, aroyl, aryloxy, arylsulfonyl, heteroaryl, heteroaryloxy, and the like; $R^8$ is selected from the group consisting of $NO_2$, OH, COOH, and the like; $R^9$ is selected from the group consisting of H, $CH_3$, and the like, or a pharmaceutically acceptable ester or salt thereof. In certain embodiments $R^6$ and $R^7$ are both halogen. In various embodiments $R^1$ and $R^4$ are both amino. In various embodiments $R^2$ and $R^3$ are both N. In various embodiments $R^8$ is $NO_2$. In certain embodiments the compound has the formula of formula II.

Also provided is a method of promoting cell death in a p53 naive cell (e.g. a cancer cell including solid tumors, metastatic cells and non-solid tumor cancers). The method typically involves contacting the cell with a compound that induces transcription of ras. In various embodiments the compound is a compound according to Formula I as described herein. In various embodiments the compound is in a pharmaceutically acceptable excipient. In certain embodiments the cell is a liver cancer cell, a breast cancer cell, a colon cancer cell, a lung cancer cell, a uterine cancer cell, an ovarian cancer cell, a prostate cancer cell, or a colon cancer cell.

Also provided is a cell line for screening for agents that promotes cell death in a p53 naive cell. The cell line typically comprises mammalian cells containing a nucleic acid construct comprising bax promoter elements comprising a 5' UTR, a TATAA sequence, and one or more consensus sequences that bind p53, where the bax promoter elements are operably linked to a reporter such that binding of a p53 protein to one or more of said consensus sequences induces or increases transcription of said reporter. In certain embodiments the reporter is a fluorescent protein, luciferase, chloramphenicol acetyl transferase (CAT), β-galactosidase (β-gal), alkaline phosphatase, horse radish peroxidase (HRP), or a growth hormone (GH). In certain embodiments the reporter comprises a luciferin gene or cDNA. In various embodiments the mammalian cell is a p53 naïve cell (e.g., a HEK293T cell).

This invention also provides methods of identifying agents that promote cell death in p53 naive cells. The methods typically involve contacting one or more cells from the cell line described herein with one or more test agents; detecting a signal from the reporter in the cell wherein an increase in signal from the reporter indicates that the agent is an agent that is likely to promote cell death in a p53 naive cell. In certain embodiments a plurality of test agents are contacted to said cell at the same time. In certain embodiments a single test agent is contacted to said cell. In various embodiments the increase is measured relative to a control lacking the test agent or comprising the test agent at a lower concentration. In certain embodiments the method is performed by a robotic system. In various embodiments the test agents are from a library selected from the group consisting of Chem Bridge DiverSet E, Bionet 1, CEREP, Maybridge 1, Maybridge 2, Peakdale 1, Peakdale 2, ChemDiv Combilab and International, Mixed Commercial Plate 1, Mixed Commercial Plate 2, Mixed Commercial Plate 3, Mixed Commercial Plate 4, ChemBridge Microformat, Commercial Diversity Set1, NCI Structural Diversity Set version 1, NCI Structural Diversity Set version 2, NCI Mechanistic Diversity Set, NCI Open Collection 1, NCI Open Collection 2, NINDS Custom Collection, SpecPlus Collection, BIOMOL ICCB Known Bioactives, ICCB Discretes Collections, ICCB2, ICCB3, ICCB4, NCI Marine Extracts, Aqueous fractions—NCI Plant and Fungal Extracts, Organic fractions—NCI Plant and Fungal Extracts, Philippines Plant Extracts 1, Philippines Plant Extracts 2, and Starr Foundation Extracts 1.

Definitions

A "p53 naive cell" refers to a cell that expresses a defective p53, and/or a p53 with reduced activity, and/or that under expresses normal p53, etc. Typically p53 naive cells show reduced p53 tumor suppressor activity as compared to a "normal" cell.

The terms "reporter" or "reporter gene" refer to gene or cDNA that expresses a product that is detectable by spectroscopic, photochemical, biochemical, immunochemical, electrical, optical, and/or chemical means. Useful reporters/labels in this regard include, but are not limited to luminescent proteins, fluorescent proteins (e.g. green fluorescent protein (GFP), red fluorescent protein (RFP), etc.), enzymes (e.g., horse radish peroxidase, alkaline phosphatase, β-galactosidase, and others commonly used in an ELISA), and the like.

The term "reporter gene operably linked to a promoter" refers to a promoter and a reporter gene disposed such that the promoter regulates transcription of the reporter gene.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

BRIEF DESCRIPTION OF THE DRAWINGS

FIG. 1 illustrates p53 binding elements in the Bax 5' UTR (SEQ ID NO:1). After the abstract, insert the accompanying Sequence Listing (pages 1-2).

FIG. 10 shows that G6 treatment of nude mice implanted with human osteosarcoma tissue results in complete regression of tumor.

DETAILED DESCRIPTION

This invention is based in part, on the idea that screening for small molecular compounds that act as p53 mimics in activating bax expression can yield therapeutics for many mammary neoplasias.

I. Screening System for p53 Mimetics/Agonists

Figure 5:
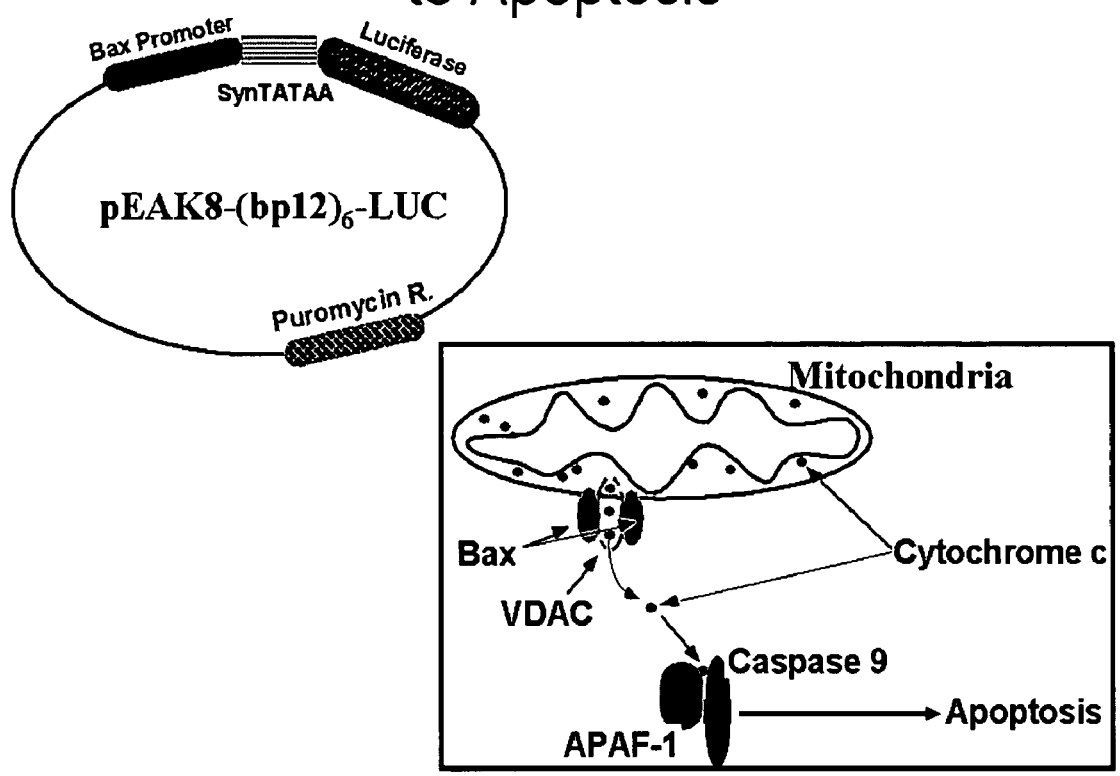
FIG. 5 illustrates that bax expression is induced by p53 and leads to apoptosis.
Figure 6:
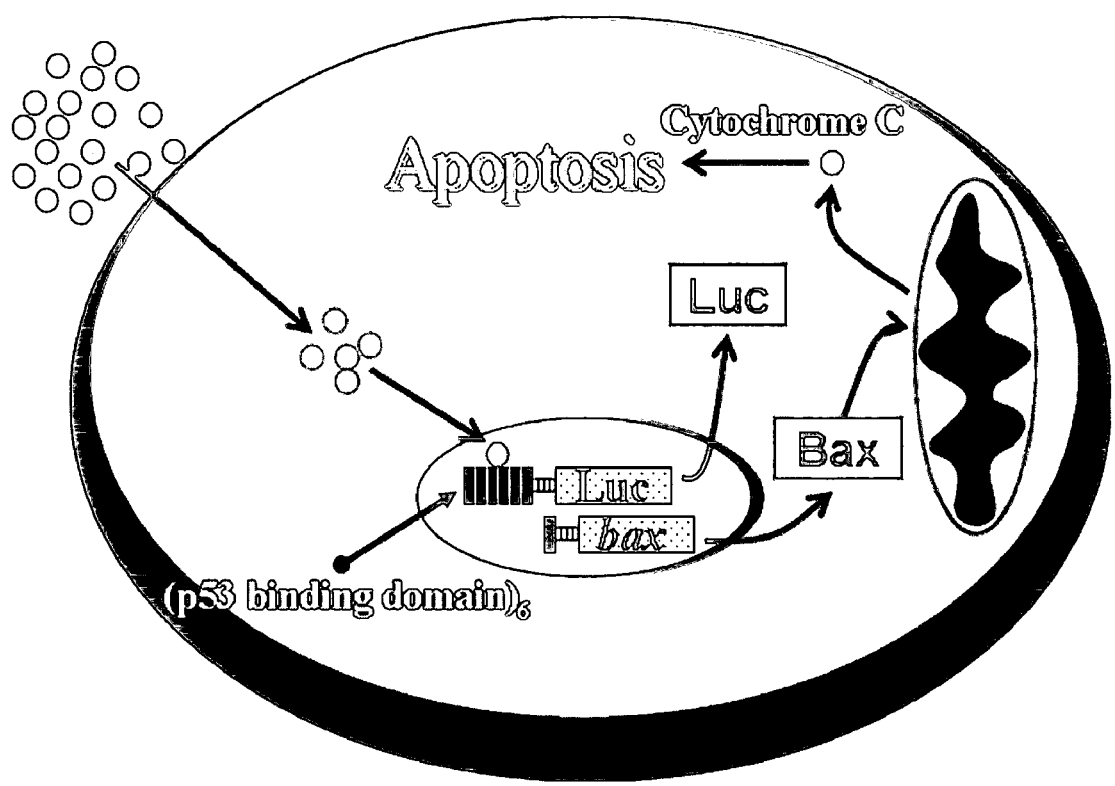
FIG. 6 illustrates screening for p53 mimetics/agonists.

To identify p53 mimics, we developed a live mammalian cell system that reports the promotion of the expression of the pro-apoptotic Bax protein. The bax promoter consists of a 372 nucleotide 5' UTR, a TATAA sequence, and several consensus sequences that bind p53, resulting in up-regulation of Bax expression (see, e.g., FIG. 1). By expressing these sites upstream of the gene encoding luciferase in HEK293T cells (see, e.g., FIG. 5), we have established a novel set of reporter cell lines. These cells provide a system which allows identification of both direct activators of Bax expression and replacements of an apoptotic function of p53 (see, e.g., FIG. 6).

A) High Throuthput Screening for P53 Mimetics/Agonists.

The cell lines described herein are particularly effective for screening for p53 mimetics/agonists. In addition, these cell lines are also well suited to "high-throughput" modalities. Conventionally, new chemical entities with useful properties (e.g., modulation of transporter activity or expression, or ability to be transported by the transporters of this invention) are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of compounds (candidate compounds/test agents) potentially having the desired activity. Such "chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

1) Libraries for Screening for Agents that Act as p53 Mimetics/Agonists.

The likelihood of an assay identifying an agent that acts as a p53 mimetic/agonist is increased when the number and types of test agents used in the screening system is increased. Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233-1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487-493, Houghton et al. (1991) *Nature*, 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909-6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217-9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology*, 14(3): 309-314), and PCT/US96/10287), carbohydrate libraries (see, e.g., Liang et al. (1996) *Science*, 274: 1520-1522, and U.S. Pat. No. 5,593,853), and small organic molecule libraries (see, e.g., benzodiazepines, Baum (1993) C&EN, Jan 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. Nos. 5,506,337, benzodiazepines 5,288,514, and the like).

In addition, a number of libraries are commercially available. Such libraries include, but are not limited to the Chem Bridge DiverSet E (16,320 compounds), •Bionet 1 (4,800 compounds), CEREP (4,800 compounds), Maybridge 1 (8,800 compounds), Maybridge 2 (704 compounds), Peakdale 1 (2,816 compounds), Peakdale 2 (352 compounds), ChemDiv Combilab and International (28,864 compounds), Mixed Commercial Plate 1 (352 compounds), Mixed Commercial Plate 2 (320 compounds), Mixed Commercial Plate 3 (251 compounds), Mixed Commercial Plate 4 (331 compounds), ChemBridge Microformat (50,000 compounds), Commercial Diversity Set1 (5,056 compounds), various NCI collections (e.g. Structural Diversity Set, version 1 (1,900 compounds), Structural Diversity Set, version 2 (1,900 compounds), Mechanistic Diversity Set (879 compounds), Open Collection 1 (90,000 compounds), Open Collection 2 (10,240 compounds), and the like, NINDS Custom Collection (1,040 compounds), ICCB Bioactives 1 (489 compounds), SpecPlus Collection (960 compounds), BIOMOL ICCB Known Bioactives (480 compounds), various ICCB Discretes Collections (e.g., ICCB1 (190 compounds), ICCB2 (352 compounds), ICCB3 (352 compounds), ICCB4 (352 compounds), and the like), various natural product extracts (e.g., NCI Marine Extracts (352 wells), Aqueous fractions—NCI Plant and Fungal Extracts (2,112 wells), Organic fractions—NCI Plant and Fungal Extracts (1,408 wells), Philippines Plant Extracts 1 (200 wells), Philippines Plant Extracts 2 (648 wells), Starr Foundation Extracts 1 (1024 wells)) and the like.

2) High Throuput Screening Devices.

A number of high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

II. P53 Mimetics/Agonists.

In certain embodiments, this invention provides a number of p53 mimetics/agonists. These compounds typically promote cell death in a p53 naive cell (e.g. a cancer cell). In certain embodiments, the compounds comprising the formula:

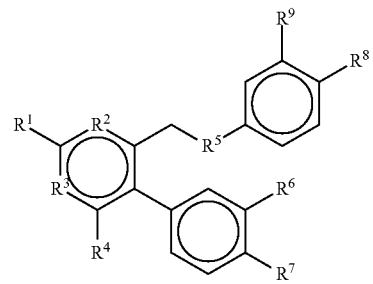

where $R^1$ and $R^4$ are independently selected from the group consisting of an amino group, a cyano group, a nitro group, a carboxyl group, halo, hydroxyl, $SO_2$, $C_{1-6}$ alkyl, $C_{1-6}$ haloalkyl, $C_{1-8}$ alkoxyl, $C_{1-11}$ alkoxyalkyl, $C_{1-6}$ alkylamino, and $C_{1-6}$ aminoalkyl; $R^2$ and $R^3$ are independently selected from the group consisting of CH, N; $R^5$ is $CH_2$ or O; $R^6$ and $R^7$ are independently selected from the group consisting of H, halogen, CN, $NO_2$, $C_{1-10}$ branched or unbranched saturated or unsaturated alkyl, $C_{1-10}$ branched or unbranched alkoxy, $C_{1-10}$ branched or unbranched acyl, $C_{1-10}$ branched or unbranched acyloxy, $C_{1-10}$ branched or unbranched alkylthio, aminosulfonyl, aryl, aroyl, aryloxy, arylsulfonyl, heteroaryl and heteroaryloxy; $R^8$ is selected from the group consisting of $NO_2$, OH, COOH; $R^9$ is selected from the group consisting of H, $CH_3$. Also included are pharmaceutically acceptable esters or salts of such compounds. In certain embodiments, $R^6$ and $R^7$ are both halogen. In certain embodiments, $R^1$ and $R^4$ are both amino. In certain embodiments, $R^3$ and $R^3$ are both N. In certain embodiments, $R^5$ is $NO_2$. In certain embodiments, the compound has the formula:

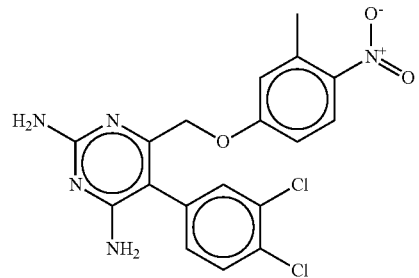

Such compounds can readily be formulated, e.g. using the compound of formula II as a starting point.

III. Pharmaceutical Formulations.

In certain embodiments, the p53 mimetics/agonists of this invention are provided and/or administered as pharmaceutical formulations. Typically one or more p53 mimetics/agonists of this invention are administered, e.g. to an individual diagnosed as having one or more symptoms of cancer. The p53 mimetics/agonists can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

For example, acid addition salts are prepared from the free base using conventional methodology that typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the p53 mimetics/agonists are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The mimetics/agonists identified herein are useful for parenteral, topical, oral, nasal (or otherwise inhaled), rectal, or local administration, such as by aerosol or transdermally, for prophylactic and/or therapeutic treatment of atherosclerosis and/or symptoms thereof. The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The mimetics/agonists of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the compositions of this invention are administered to a patient suffering from one or more symptoms of atherosclerosis or at risk for atherosclerosis in an amount sufficient to cure or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of p53 mimetics/agonists can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. It will be appreciated that such dosages may be varied to optimize a therapeutic regimen in a particular subject or group of subjects.

In certain preferred embodiments, the p53 mimetics/agonists of this invention are administered orally (e.g. via a tablet) or as an injectable in accordance with standard methods well known to those of skill in the art. In other preferred embodiments, the p53 mimetics/agonists, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

In certain instances, particularly where bioavailability is low with systemic administration, the p53 mimetics/agonists are administered directly to a tumor site or to a post-operative tumor site. Such delivery may be direct through a cannula or by injection or placement of a time-release formulation, e.g. during a surgical procedure.

Other preferred formulations for topical drug delivery include, but are not limited to, ointments and creams. Ointments are semisolid preparations which are typically based on petrolatum or other petroleum derivatives. Creams containing the selected active agent, are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

IV. Mitigation/Treatment of Cancers.

In certain instances the p53 mimetics/agonists of this invention are administered to mitigate one or more symptoms of a cancer (e.g., to induce cell death in cancer cells). The p53 mimetics/agonists can be administered to reduce tumor growth/proliferation, to inhibit metastasis, to prevent relapse (e.g. after surgery, radiotherapy, etc.), or as a component of a multiple-modality therapy.

Typically the p53 mimetics/agonists will be administered in an amount sufficient to produce a biological effect (e.g., to inhibit cancer cell growth and/or proliferation). Greatest efficacy is expected to be found in cancers characterized by p53 naïve cells.

V. Kits.

In still another embodiment, this invention provides kits for screening for p53 mimetics/agonists. Such kits typically comprise a container containing a cell line as described herein.

In other embodiments, this invention provides kits promoting cell death in a p53 naïve cell. These kits typically comprise a container containing one or more of the p53 mimetics/agonists of this invention.

The kits may optionally include one or more reagents for use in the methods of this invention. Such "reagents" may include, but are not limited to, cells and/or cell lines, transfection reagents (e.g. $CaPO_4$, lipofectin), detectable labels, means for detecting labels, buffers, anti-transporter antibodies, nucleic acid constructs encoding housekeeping genes, bioreactors, syringes, and other devices.

In addition, the kits may include instructional materials containing directions (i.e., protocols) for the practice of the methods of this invention. Certain preferred instructional materials provide protocols utilizing the kit contents for screening for p53 mimetics/agonists or for promoting cell death in p53 naïve cells. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Identification of P53 Mimetics

To identify p53 mimics, we developed a live mammalian cell system that reports the promotion of the expression of the pro-apoptotic Bax protein. The bax promoter consists of a 372 nucleotide 5' UTR, a TATAA sequence, and several consensus sequences that bind p53, resulting in up-regulation of Bax expression (see, e.g., FIG. 1). By expressing these sites upstream of the gene encoding luciferase in HEK293T cells, we have established a novel set of reporter cell lines. These cells provide a system which allows identification of both direct activators of Bax expression and replacements of an apoptotic function of p53.

Discovery of a Small Molecule that Replaces p53 Function

In initial studies, cotransfection of a p53 expression plasmid with a reporter bearing oligomerized consensus binding sites yielded strongly luminescent cells, whereas cotransfection with an irrelevant plasmid gave no luminescence. Our system shows high enough signal and low enough background to permit small molecules to be isolated from compound libraries. By employing the Multi-Probe II liquid handling robotic system and the ultra-sensitive Top-Count luminometer, high-speed screening of thousands of compounds has been enabled at the Buck Institute.

Figure 2A:
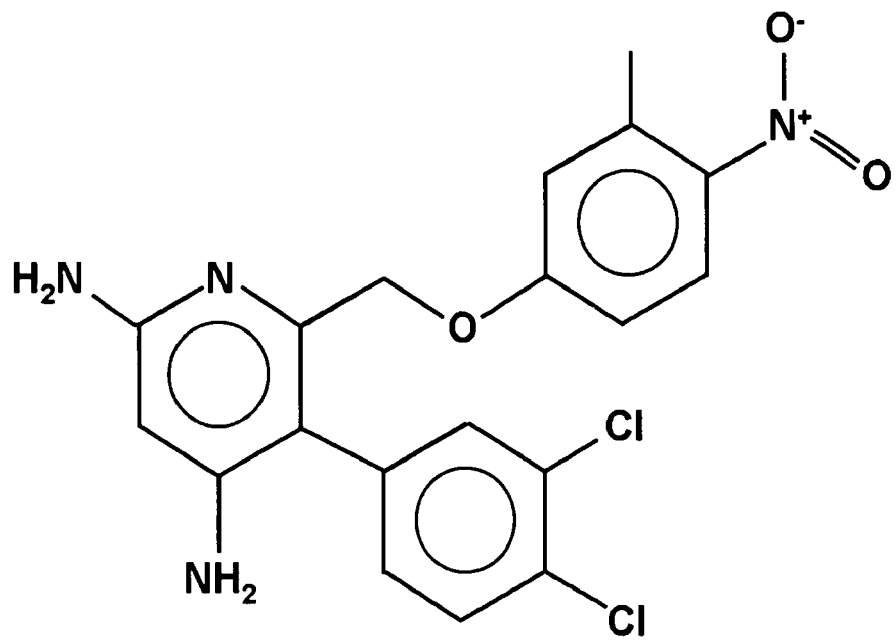
FIG. 2A shows the structure of Rp53-1 (G6).
Figure 2B:
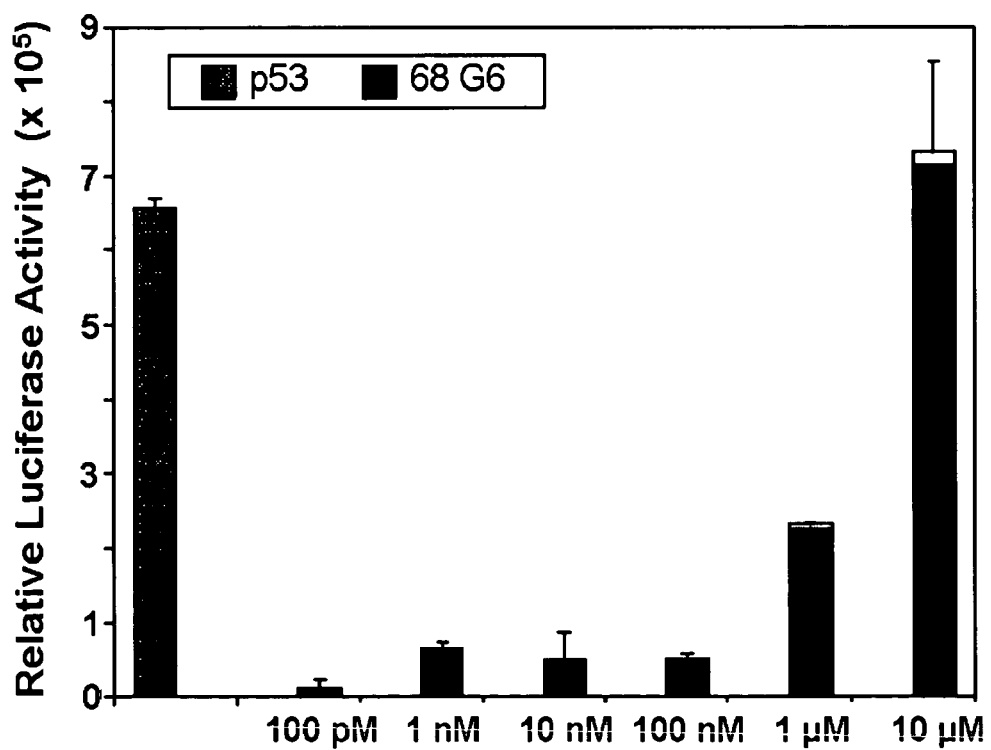
FIG. 2B shows that Rp53-1 (G6) activates the p53/Bax reporter in HEK293T cells to levels relative to transiently overexpressed p53.

We obtained and screened a 2000 compound small molecule library made available by the National Cancer Institute in our p53 reporter system in HEK293T cells. Surprisingly, we identified eight compounds that acted upon the p53 reporter system and yielded increases in luciferase expression and activity. One compound (dubbed Rp53-1 or G6) produced significant levels of luciferase activity, and at high concentrations (10 µM) induced expression of luciferase levels greater than transfected wild-type p53 (see, e.g., FIG. 2B).

Chemotherapeutic Agent Rp53-1 Specifically Targets Neoplasia

Figure 3:
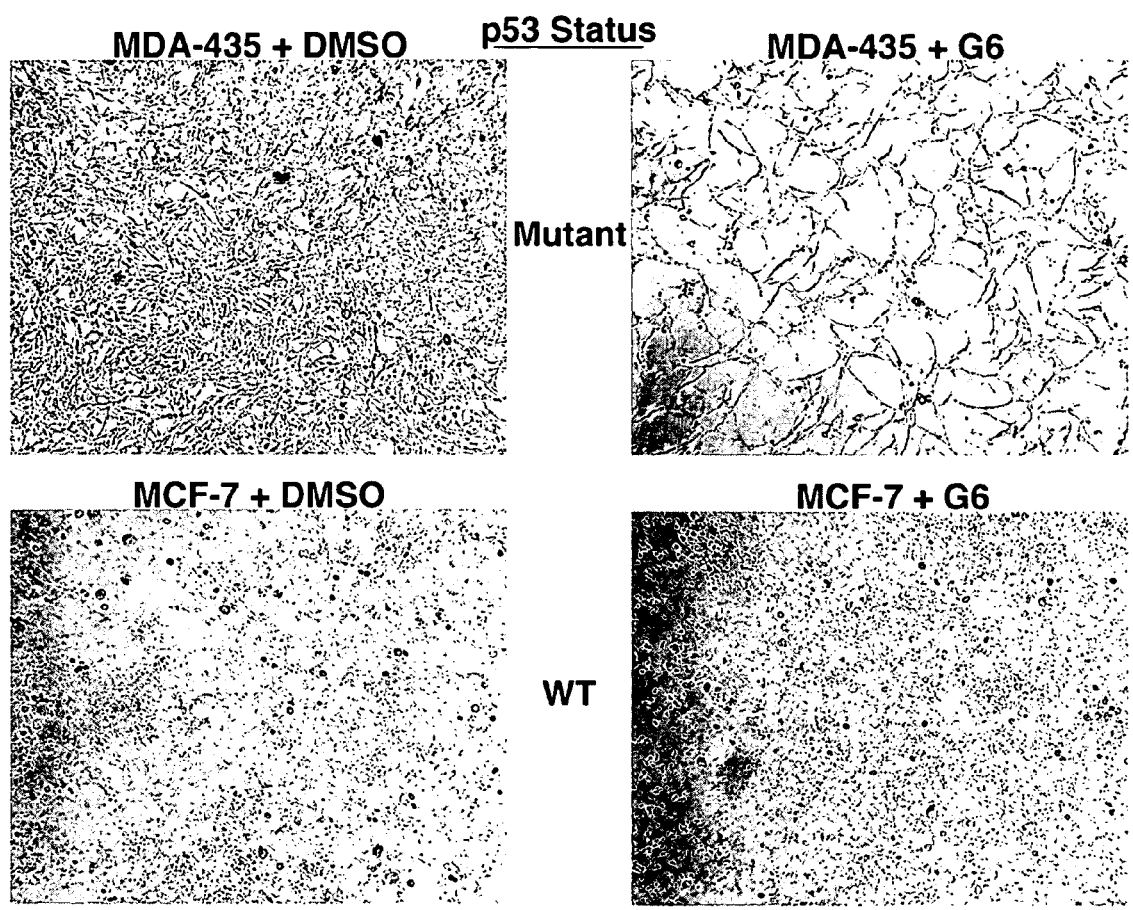
FIG. 3 shows that p53-mutant (MDA-435), but not wild-type (MCF-7), breast cancer cells are sensitive to the p53-mimetic compound Rp53-1 (G6).

To assess the ability of the small molecule compound Rp53-1 to mimic the transcription-promoting functions of p53 leading to Bax expression and induction of cell death, p53-mutated MDA-MB-435 and p53-wild-type MCF-7 human breast cancer cells were treated with Rp53-1. Interestingly only the former was sensitive to Rp53-1 (FIG. 3). Similarly, other p53-mutant tumor cell lines were also sensitive to Rp53-1 (colon: ColoHSR, SW480, HT29; prostate: PC-3, DU145; osteosarcoma: SAOS-2), whereas p53-wild-type cells were resistant (colon: Lovo; prostate: LNCaP) The specificity displayed by Rp53-1 in inducing death solely in p53-mutant cells makes it an ideal candidate for utilization as a therapeutic intervention for p53-inactive (or p53-malfunctioning) tumors (i.e., most clinically relevant tumors). Lack of toxicity in cells generating normal p53 activity (all other human cells) would reduce possible side effects.

Since p53 upregulates Bax expression while it also downregulates the related anti-apoptotic Bcl-2 (thus having at least two effects that lead to cell death), the identification of small molecules able to replace lost p53 activity by upregulating Bax, thus inducing cell death in a p53-independent fashion (i.e., inducing cell death in the absence of p53 function by replacing p53 functional activity with a small molecule) may allow the discovery of novel tools to control both Bax and Bcl-2 within tissues. The importance of these critical molecules in human neoplasia is supported by the high frequency of p53, Bax and Bcl-2 mutations in human cancers.

Conclusion

The discovery of the first p53 mimic, the active compound Rp53-1, validates and displays the potential of the methodology outlined above. The screening systems described herein significantly increase our potential to make discoveries like Rp53-1, optimize Rp53-1 for human clinical trials, and make possible a novel approach to eradicate breast cancer.

Example 2

Cancer Therapeutics Using p53 Mimetics as Activators of Bax Expression p53 mutations are associated with a high percentage of all human tumors. Using a new high-throughput small molecule screen developed here, scientists in the Buck Institute's Discovery Translation Unit (DTU) have discovered the first p53 functional mimetic called G6. G6 and related therapeutics can be developed as therapeutic agents for cancers including breast, prostate, lung, colon and pancreatic cancers as well as osteosarcoma.

Background p53 is regarded to be the "guardian of the genome." One of p53's roles is to commit genetically abnormal cells to programmed cell death thereby suppressing tumor growth. If p53 is absent or mutated to a non-functional form its key role as a tumor suppressor is eliminated, as is observed in many cancers. Activation of p53 is often necessary for sensitizing tumor cells to chemotherapy and radiation; absence of p53 function is often associated with unresponsiveness to these therapies. Over one-half of all human tumors lack proper p53 function. Not surprisingly, methods of restoring p53 function have long been sought as an anticancer strategy, however, this has proven to be a daunting problem.

Figure 4:
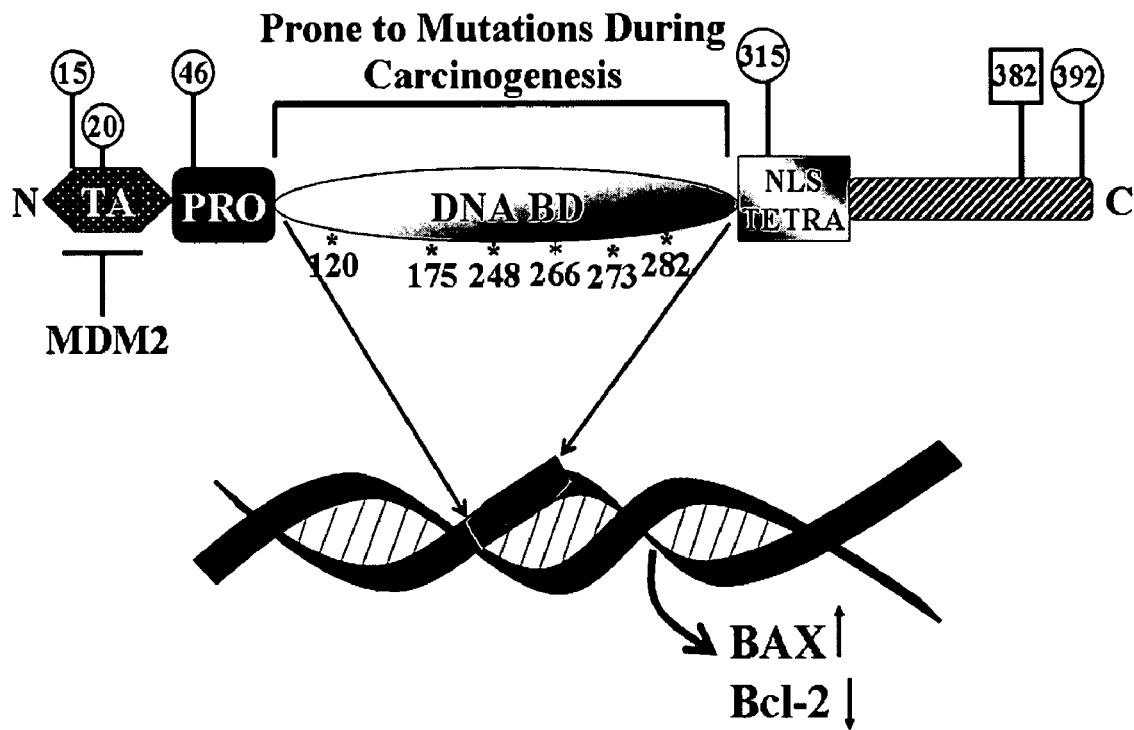
FIG. 4 illustrates p53 mutations that result in dysregulation of Bax/Bcl-2 expression.

One key function for p53 is to regulate the expression of proteins important to the life and death decisions that cells make when responding to adverse, neoplastic situations, such as deleterious mutations introduced in DNA or unwarranted increases in rate of proliferation. Activation of p53 (by modifications such as phosphorylation (FIG. 4, circle) results in alterations in the expression of such proteins as the antagonistic partners Bax and Bcl2.

In neoplastic conditions, p53 upregulates the expression of the pro-death protein Bax, while it downregulates the anti-death (oncogenic) protein Bcl2. Moreover, the only known endogenous activator of Bax expression is p53. One-third of all advanced human breast carcinomas demonstrate a marked reduction in expression of Bax. The subgroup of patients displaying reduced Bax expression generally respond poorly to therapy and exhibit rapidly growing tumors and shorter median survival. For these and other reasons, we have designed a screen for small molecule compounds that mimic the role of p53 as a retardant of oncogenesis.

The Technology

Screening for small molecule compounds that act as p53 mimics is expected to yield therapeutics for many cancers. The discovery of the first p53 functional mimic, the active compound G6 (see, e.g., FIGS. 2A and 2B) validates and displays the potential of the methodology. Utilizing a novel live-cell high-throughput screening system we determined that G6 (FIG. 2A) remediates the transcriptional activities of p53 lost in neoplasia. This "lead" compound presents the opportunity for optimization for human clinical trial in cancers which are p53 deficient or which express faulty p53. Clearly other compound families can be identified through the same screening process.

Figure 8:
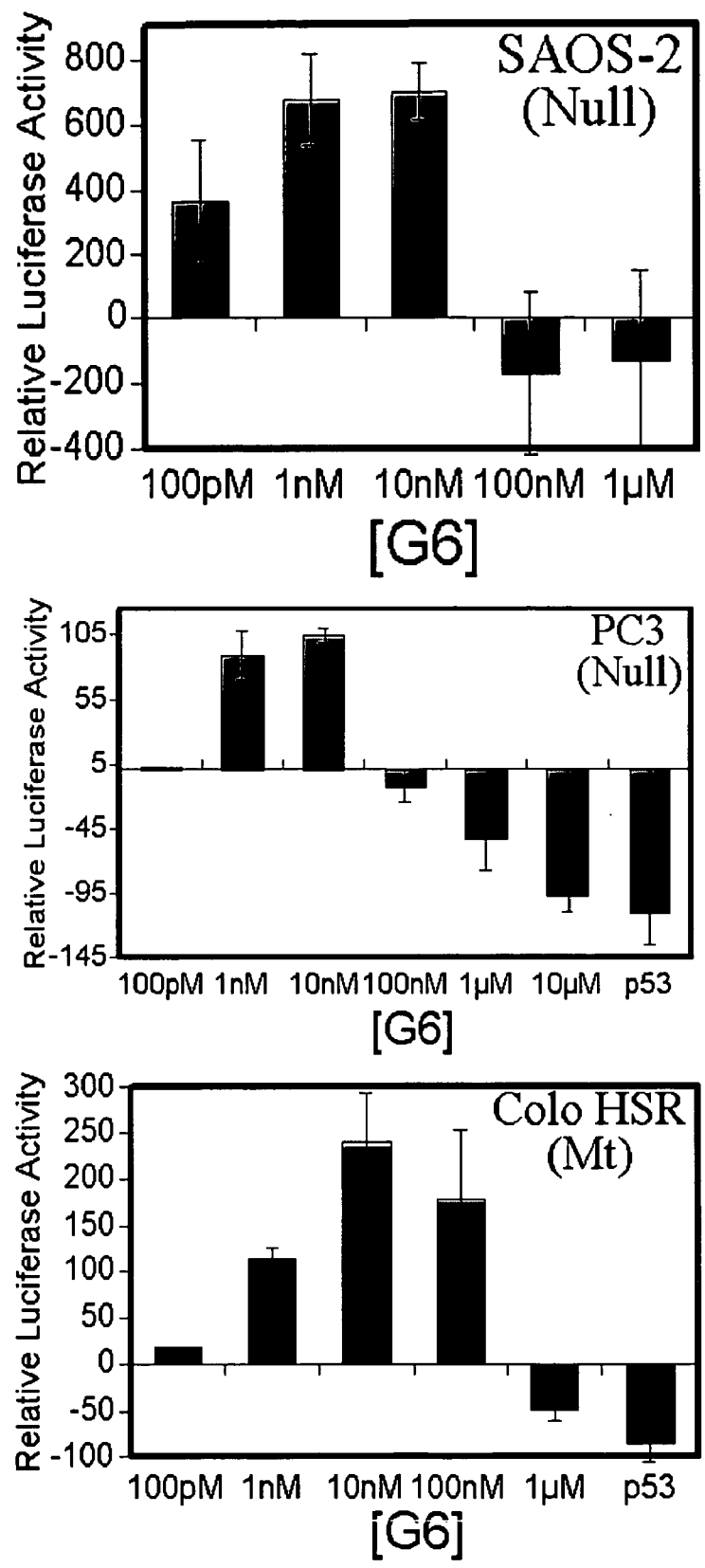
FIG. 8 shows that G6 induces p53 Reporter in p53 Mt and Null Cells.
Figure 9:
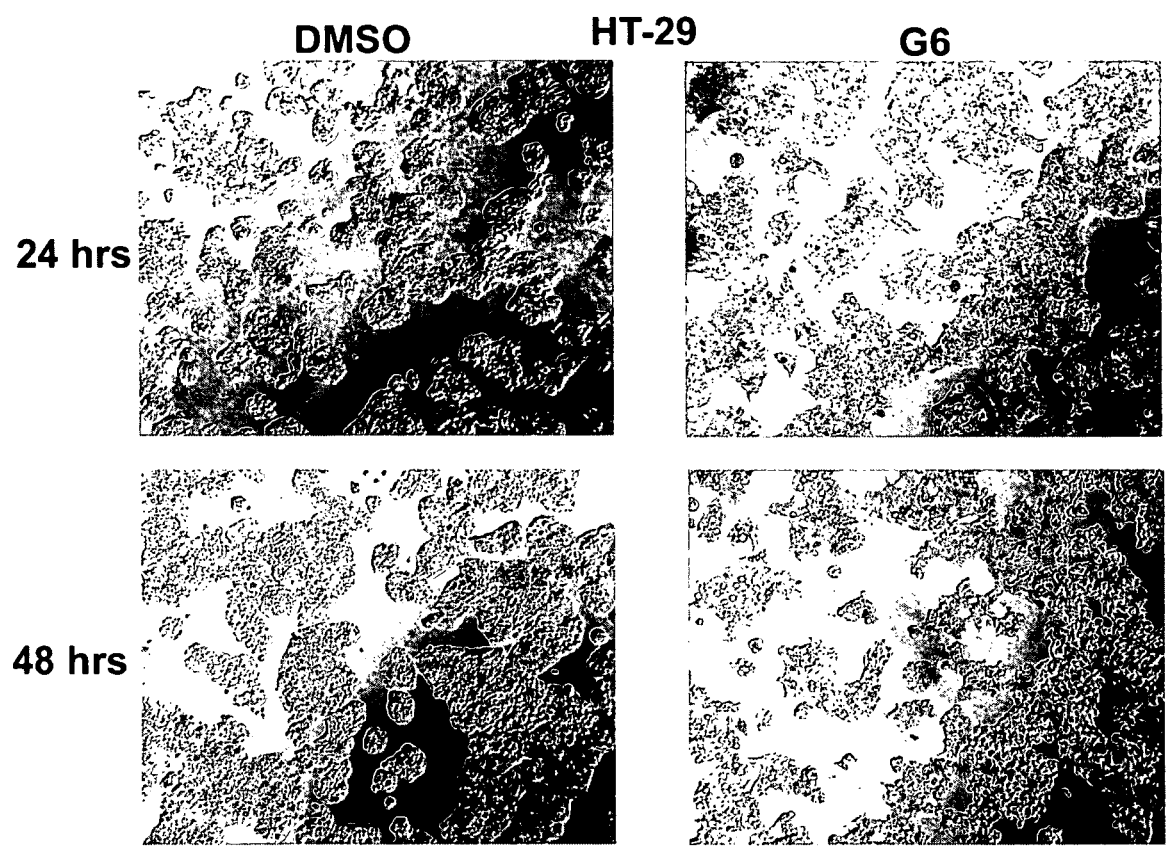
FIG. 9 illustrates the results of treatment of HT-29 cells with G6.

Inherent in the initial drug design was a strategy to develop a therapy that targets mutant p53 containing cells and that would leave healthy cells expressing normal p53 unaffected (FIG. 3). Affirming the validity of G6 as a lead compound, every p53 defective tumor cell line treated with G6 showed susceptibility, whereas wild type cells from corresponding normal tissue were unaffected thus confirming the drug's selectivity (see, e.g., Table 1, and FIGS. 8 and 9).

TABLE 1

P53 wt and null cells are sensitive to G6.

| Cell Line | P53 Status WT | P53 Status Mutant or Null | G6 Sensitivity |
|---|---|---|---|
| Prostate | | | |
| PC3 | | Null | ++ |
| DU145 | | Mt | ++ |
| LNcap | WT | | − |
| Colon | | | |
| ColoHSR | | Mt | ++++ |
| SW480 | | Mt | ++ |
| Lovo | WT | | − |
| HT29 | | Mt | ++ |
| Breast | | | |
| MDA-435 | | Mt | +++ |
| MCF-7 | WT | | − |
| Osteosarcoma | | | |
| Saos-2 | | Null | ++++ |
| Lung | | | |
| A549 | WT | | − |
| H23 | | Mt | +++ |
| Embryonic kidney | | | |
| 293 | WT | | − |

Figure 7:
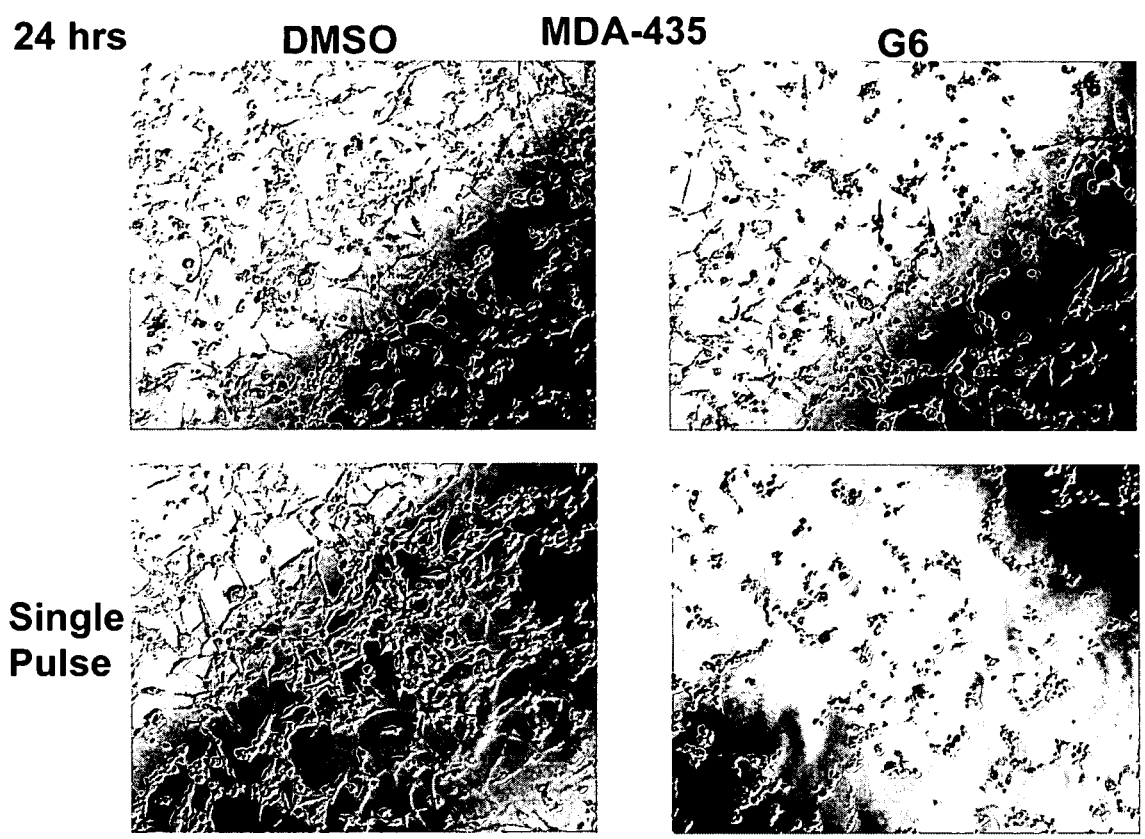
FIG. 7 shows that a single pulse treatment of breast cancer cells with G6 results in complete drug efficacy.

Since G6 activates an inherent cellular pathway, a single pulse of G6 in the nanomolar range is sufficient to activate the cell death program (FIG. 7). Thus G6 appears to be a potent treatment.

Initial trials of G6 in human osteosarcoma xenografted nude mice have shown promise (FIG. 10). Mice bearing p53 abnormal tumors have responded well to G6. Tumor regression has been complete and none of the mice have shown adverse side effects in response to treatment with G6. Further mouse studies are currently underway.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A pharmaceutical formulation that promotes cell death in a p53 naive cell, said formulation comprising a pharmacologically acceptable excipient and a therapeutically effective amount of a compound having the formula:

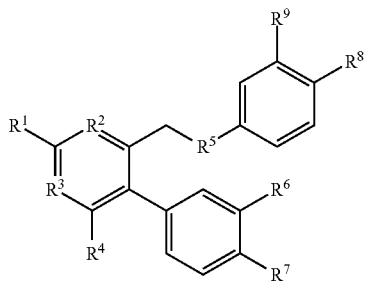

wherein:
$R^1$ and $R^4$ are independently selected from the group consisting of an amino group, a cyano group, a nitro group, a carboxyl group, halo, hydroxyl, $SO_2$, $C_{1-6}$ alkyl, $C_{1-6}$ haloalkyl, $C_{1-8}$ alkoxyl, $C_{1-11}$ alkoxyalkyl, $C_{1-6}$ alkylamino, and $C_{1-6}$ aminoalkyl;
$R^2$ and $R^3$ are independently selected from the group consisting of CH and N;
$R^5$ is $CH_2$ or O;
$R^6$ and $R^7$ are independently;
$R^8$ is selected from the group consisting of $NO_2$, OH, and COOH; and
$R^9$ is selected from the group consisting of H, $CH_3$;
or a pharmaceutically acceptable ester or salt thereof;
wherein said formulation is sterile;
and wherein said formulation is an injectable, an aerosol formulation, or an implantable sustained-release formulation.

2. The formulation of claim 1, wherein $R^1$ and $R^4$ are both amino.

3. The formulation of claim 1, wherein $R^2$ and $R^3$ are both N.

4. The formulation of claim 1, wherein $R^8$ is $NO_2$.

5. The formulation of claim 1, wherein said compound has the formula:

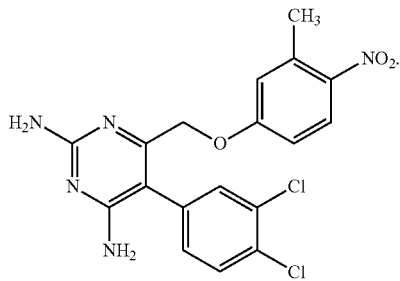

6. A pharmaceutical formulation that promotes cell death in a p53 naive cell, said formulation comprising a pharmacologically acceptable excipient and a therapeutically effective amount of a compound having the formula:

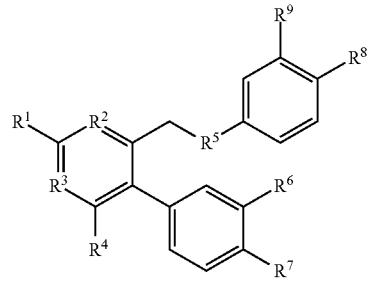

wherein:
$R^1$ and $R^4$ are independently selected from the group consisting of an amino group, a cyano group, a nitro group, a carboxyl group, halo, hydroxyl, $SO_2$, $C_{1-6}$ alkyl, $C_{1-6}$ haloalkyl, $C_{1-8}$ alkoxyl, $C_{1-11}$ alkoxyalkyl, $C_{1-6}$ alkylamino, and $C_{1-6}$ aminoalkyl;
$R^2$ and $R^3$ are independently selected from the group consisting of CH and N;
$R^5$ is $CH_2$ or O;
$R^6$ is selected from the group consisting of halogen, CN, $NO_2$, $C_{1-10}$ branched or unbranched saturated or unsaturated alkyl, $C_{1-10}$ branched or unbranched alkoxy, $C_{1-10}$ branched or unbranched acyl, $C_{1-10}$ branched or unbranched acyloxy, $C_{1-10}$ branched or unbranched alkylthio, aminosulfonyl, aryl, aroyl, aryloxy, arylsulfonyl, heteroaryl and heteroaryloxy;
$R^7$ is selected from the group consisting of H, halogen, CN, $NO_2$, $C_{1-10}$ branched or unbranched saturated or unsaturated alkyl, $C_{1-10}$ branched or unbranched alkoxy, $C_{1-10}$ branched or unbranched acyl, $C_{1-10}$ branched or unbranched acyloxy, $C_{1-10}$ branched or unbranched alkylthio, aminosulfonyl, aryl, aroyl, aryloxy, arylsulfonyl, heteroaryl and heteroaryloxy;
$R^8$ is selected from the group consisting of $NO_2$, OH, and COOH; and
$R^9$ is $CH_3$;
or a pharmaceutically acceptable ester or salt thereof;
wherein said formulation is sterile;
and wherein said formulation is an injectable, an aerosol formulation, or an implantable sustained-release formulation.

7. The formulation of claim 6, wherein $R^6$ and $R^7$ are both halogen.

8. The formulation of claim 6, wherein $R^1$ and $R^4$ are both amino.

9. The formulation of claim 6, wherein $R^2$ and $R^3$ are both N.

10. The formulation of claim 6, wherein $R^8$ is $NO_2$.

11. The formulation of claim 1, wherein the p53 naive cell is a cancer cell.

12. The formulation of claim 6, wherein the p53 naive cell is a cancer cell.

* * * * *

SEQUENCE LISTING

<160> NUMBER OF SEQ ID NOS: 1

<210> SEQ ID NO 1
<211> LENGTH: 975
<212> TYPE: DNA
<213> ORGANISM: Homo sapiens

<400> SEQUENCE: 1

```
cctgctgatc tatcagcaca gattagtttc tgccactttt taaacttcat attccttttc      60
tttttacaca aacacaaaca ttcgagtcat gactgggtgg ggtggctcaa gcctgtaatc     120
tcagcacttt gggaggccaa ggtgcgagga tgcttgagtc tgggagttca gagaccagcc     180
tgggcaacat agagagacct catctccaca taaaaagttt taaaaattaa ccaggggcgg     240
tgtagtccca gctactcagg aggctgaggt gggaggcttc agcccgggaa ttccagactg     300
cagtgagcca tgattgggcc actgcactcc agcctgggca acacagtgag accctgtctc     360
aaaaaaaaaa aaaaaaaaaa aaaaaaaaac aggaaaaaac aaacaaacag aaaagcaggc     420
ctggcgcggt agctcatgcc tgtaatccca gcgctttgga aggctgagac ggggttatct     480
cttgggctca caagttagag acaagcctgg gcgtgggcta tattgctaga tccaggtctc     540
tgcaaaaaac aaaaccactc agtttttagt catctataac gtcctgcctg gaagcatgct     600
attttgggcc tctgagcttt tgcacttgct aattccttct gcgctgggga gagctcaaac     660
cctgcccgaa acttctaaaa atggtgcctg gataaatgaa ggcattagag ctgcgattgg     720
acgggcggct gttggacggc gccactgctg gcacttatcg ggagatgctc attggacagt     780
cacgtgacgg gaccaaacct cccgagggag cgaggcaggt gcggtcacgt gacccggcgg     840
cgctgcgggg cagcggccat tttgcggggc ggccacgtga aggacgcacg ttcagcgggg     900
ctctcacgtg acccgggcgc gctgcggccg cccgcgcgga cccggcgaga ggcggcggcg     960
ggagcggcgg tgatg                                                      975
```